(12) United States Patent
Leng et al.

(10) Patent No.: US 12,239,305 B2
(45) Date of Patent: Mar. 4, 2025

(54) CHANNEL DEVICE FOR SURGERY AND TRIGGER STRUCTURE

(71) Applicant: Micro-Tech Nuroway Co., Ltd., Nanjing (CN)

(72) Inventors: Derong Leng, Jiangsu (CN); Zhuhai Lv, Jiangsu (CN); Wenqi Lv, Jiangsu (CN); Changqing Li, Jiangsu (CN); Long Long, Jiangsu (CN); Jianyu Wei, Jiangsu (CN); Chengwei Tang, Jiangsu (CN); Li Ding, Jiangsu (CN)

(73) Assignee: Micro-Tech Nuroway Co., Ltd., Jiangsu (CN)

( * ) Notice: Subject to any disclaimer, the term of this patent is extended or adjusted under 35 U.S.C. 154(b) by 891 days.

(21) Appl. No.: 17/310,195

(22) PCT Filed: Apr. 15, 2020

(86) PCT No.: PCT/CN2020/084867
§ 371 (c)(1),
(2) Date: Jul. 26, 2021

(87) PCT Pub. No.: WO2021/189567
PCT Pub. Date: Sep. 30, 2021

(65) Prior Publication Data
US 2022/0304669 A1    Sep. 29, 2022

(30) Foreign Application Priority Data
Mar. 26, 2020    (CN) .......................... 202010224883.X

(51) Int. Cl.
*A61B 17/02*    (2006.01)
*A61B 90/00*    (2016.01)
(Continued)

(52) U.S. Cl.
CPC .......... *A61B 17/0218* (2013.01); *A61B 90/08* (2016.02); *A61B 2017/0034* (2013.01);
(Continued)

(58) Field of Classification Search
CPC ................ A61B 17/02; A61B 17/0217; A61B 2017/0034; A61B 2017/00367
(Continued)

(56) References Cited

U.S. PATENT DOCUMENTS 10,136,881 B2 * 11/2018 Mariani ............. A61B 17/0218
2016/0278756 A1 * 9/2016 Aho .................... A61B 17/0218

FOREIGN PATENT DOCUMENTS

CN    101138509 A    3/2008
CN    101790352 A    7/2010
(Continued)

OTHER PUBLICATIONS

International Search Report for corresponding PCT/CN2020/084867, issued Dec. 25, 2020, 5pp.
(Continued)

*Primary Examiner* — Eduardo C Robert
*Assistant Examiner* — Christina Negrellirodriguez
(74) *Attorney, Agent, or Firm* — Wolter Van Dyke Davis, PLLC; Eugene J. Molinelli; Michael W. Taylor

(57) ABSTRACT

Disclosed are a channel device for surgery and a trigger structure. It aims at improving the problem that the operational efficiency of existing channel devices for surgery is not high. The channel device for surgery includes: a binding cord configured to be wound around a metal net; and a binding wire configured to pass through the binding cord and tighten up the binding cord, so as to compress the metal net, or configured to be pulled away from the binding cord, so as to loosen the binding cord and the metal net. In the trigger structure, different first locking portions are config-
(Continued)

ured to cooperate with a first engaging portion, so as to drive the trolley to slide intermittently relative to the handle, such that a second engaging portion cooperates with different second locking portions, hereby locking the sliding trolley in different positions on the handle.

20 Claims, 5 Drawing Sheets

(51) Int. Cl.
*A61B 17/00* (2006.01)
*A61B 17/34* (2006.01)

(52) U.S. Cl.
CPC ............... *A61B 2017/00367* (2013.01); *A61B 2017/00407* (2013.01); *A61B 2017/0042* (2013.01); *A61B 2017/0046* (2013.01); *A61B 2017/0225* (2013.01); *A61B 2017/3454* (2013.01)

(58) Field of Classification Search
USPC .......................................................... 600/206
See application file for complete search history.

(56) References Cited

FOREIGN PATENT DOCUMENTS

| CN | 104095608 A | 10/2014 |
|---|---|---|
| CN | 104473666 A | 4/2015 |

OTHER PUBLICATIONS

Written Opinion of the International Searching Authority for corresponding PCT/CN2020/084867, issued Dec. 25, 2020, 4pp.

\* cited by examiner

CHANNEL DEVICE FOR SURGERY AND TRIGGER STRUCTURE

CROSS-REFERENCE TO RELATED APPLICATIONS

The present disclosure claims the priority of the Chinese Patent Application No. CN202010224883.X, entitled "Channel Device for Surgery and Trigger Structure", filed with the Chinese Patent Office on Mar. 26, 2020, the entity of which is incorporated herein by reference.

TECHNICAL FIELD

The present disclosure pertains to channel device for use in neurological surgical procedures, and particularly to a channel device for surgery and a trigger structure.

BACKGROUND

At present, neurosurgical operative passage is formed mainly through incision of the cerebral cortex and fistulization, hereby forming a surgical channel; a surgical channel may also be formed through incision of the cerebral cortex and traction using a retractor; and it is also possible to form an channel by placing a brain retractor having a fixed geometry after the incision of the cerebral cortex or by placing an X-ray film with finger stalls of a glove after the incision of the cerebral cortex during surgery. At present, surgical channel devices commonly used in clinical practice include brain spatulas and double-layered transparent sleeves and so on. The above-mentioned methods and devices thereof all cause cutting damages to brain tissue, and cause damages to brain tissue fibers, blood vessel damages, and brain function damages.

An channel device is provided in the prior art, wherein a surgical channel is formed through traction of brain tissue after puncturing into the brain tissue, relying on its own elasticity and flexibility, wherein the incision of the cerebral cortex is unnecessary, avoiding damages to brain tissue fibers, blood vessel damages and brain function damages; accordingly, a minimally invasive surgical passage is realized in its true sense, and the substantial damage is just the damage of a puncture passage.

However, existing channel devices have the problem of low operational efficiency.

SUMMARY

An object of the present disclosure comprises, for example, providing a channel device for surgery, which can improve the problem that the operational efficiency of existing channel devices for surgery is not high.

The object of the present disclosure further comprises, for example, providing a trigger structure, which can improve the problem that the operational efficiency of existing channel devices for surgery is not high.

An embodiment of the present disclosure may be implemented as follows.

The embodiment of the present disclosure provides a channel device for surgery, comprising, a retractor, including a metal net configured to form a surgical channel; a conveyor, wherein the distal end of the conveyor has an openable channel configured for placing the metal net; a binding cord, configured to be wound around the metal net; and a binding wire, configured to pass through the binding cord and tighten up the binding cord, so as to compress the metal net, or configured to be pulled away from the binding cord, so as to loosen the binding cord and the metal net.

Optionally, the binding cord is configured to sequentially pass through a plurality of meshes at the distal end of the metal net, so as to form a plurality of loop holes with the metal net, with the plurality of loop holes being distributed along a circumferential direction of the metal net.

Optionally, the binding wire is configured to sequentially pass through the plurality of loop holes and to tighten up the binding cord when the binding wire is in a straightened state.

Optionally, the conveyor includes a puncture head provided with a first hole in communication with the channel, when the binding wire is in the straightened state, the distal end of the binding wire is accommodated in the first hole, and the proximal end of the binding wire extends in a direction away from the first hole, so as to be configured to move under the action of an external force, and accordingly pull the binding wire away from the binding cord.

Optionally, the conveyor further includes a fixing block, which is fixed in the channel and provided with a limit hole; and the binding wire is configured to pass movably through the limit hole and is positionally limited by means of the fixing block.

Optionally, the fixing block is arranged at the distal end of the channel, and is located on the inner side of the metal net, so as to be configured to prevent the metal net from moving towards the proximal end of the channel.

Optionally, the puncture head is provided with an injection hole communicating the channel and the exterior; the conveyor further includes a supporting tube and a Luer taper, wherein the supporting tube is arranged within the channel, and the distal end of the supporting tube is in connection with the puncture head and is in communication with the injection hole; and the Luer taper is in communication with the supporting tube.

Optionally, the conveyor further includes a snap ring, which is in connection with the binding wire, so as to be configured to pull the binding wire away from the binding cord under the action of an external force.

Optionally, the conveyor further includes a damping portion, and the snap ring is configured to be clamped with or disengaged from the damping portion; when the snap ring is disengaged from the clamping portion, the snap ring is configured to pull the binding wire away from the binding cord under the action of an external force.

Optionally, the damping portion is column-shaped; and the snap ring includes a semicircular ring and a toggle handle which are in connection with each other, wherein the semicircular ring is configured to be clamped with or disengaged from the external wall of the damping portion.

Optionally, the conveyor further includes an outer tube and a trigger structure, which includes a trolley, a trigger, and a handle, wherein the trigger and the trolley are commonly slidably arranged on the handle, the trolley is in connection with the outer tube, and the outer tube is driven to move so as to open the channel when the trolley slides relative to the handle; the trolley is provided with a first engaging portion and a second engaging portion; the trigger is provided with a first locking portion, and there is a plurality of first locking portions; the handle is provided with a second locking portion, and there is a plurality of second locking portions; and different first locking portions are configured to cooperate with the first engaging portion, so as to drive the trolley to slide intermittently relative to the handle, such that the second engaging portion cooperates with different second locking portions, hereby locking the sliding trolley in different positions on the handle.

Optionally, the first locking portion is configured to be in locking cooperation with the first engaging portion, when the trigger slides relative to the handle in a first direction, such that the trigger pushes the trolley to slide in the first direction; and the first locking portion is configured to be in slidable cooperation with the first engaging portion, when the trigger slides relative to the handle in a second direction, wherein the trolley is fixed relative to the handle, when the first locking portion is in slidable cooperation with the first engaging portion, wherein the first direction is opposite to the second direction.

Optionally, the trigger structure further includes a reset member, wherein the reset member is connected between the trigger and the handle, such that the trigger has a tendency to slide relative to the handle in the second direction.

Optionally, the first locking portion is a first unidirectional tooth arranged to protrude from the trigger; and the second locking portion is a second unidirectional tooth arranged to protrude from the handle.

Optionally, the first engaging portion is a first elastic piece, with one end of the first elastic piece being connected on the trolley, while the other end of the first elastic piece being configured to be in locking cooperation with the first unidirectional tooth when moving in the first direction, and to be in slidable cooperation with the first unidirectional tooth when moving in the second direction; and the second engaging portion is a second elastic piece, with one end of the second elastic piece being connected on the trolley, while the other end of the second elastic piece being configured to be in locking cooperation with the second unidirectional tooth when moving in the first direction, and to be in slidable cooperation with the second unidirectional tooth when moving in the second direction.

An embodiment of the present disclosure further provides a trigger structure, comprising: a trolley, a trigger, and a handle, wherein the trigger and the trolley are commonly slidably arranged on the handle; the trolley is provided with a first engaging portion and a second engaging portion; the trigger is provided with a first locking portion, and there is a plurality of first locking portions; the handle is provided with a second locking portion, and there is a plurality of second locking portions; and different first locking portions are configured to cooperate with the first engaging portion, so as to drive the trolley to slide intermittently relative to the handle, such that the second engaging portion cooperates with different second locking portions, hereby locking the sliding trolley in different positions on the handle.

Optionally, the first locking portion is configured to be in locking cooperation with the first engaging portion, when the trigger slides relative to the handle in a first direction, such that the trigger pushes the trolley to slide in the first direction; and the first locking portion is configured to be in slidable cooperation with the first engaging portion, when the trigger slides relative to the handle in a second direction, wherein the trolley is fixed relative to the handle, when the first locking portion is in slidable cooperation with the first engaging portion, wherein the first direction is opposite to the second direction.

Optionally, the trigger structure further includes a reset member, wherein the reset member is connected between the trigger and the handle, such that the trigger has a tendency to slide relative to the handle in the second direction.

Optionally, the first locking portion is a first unidirectional tooth arranged to protrude from the trigger; and the second locking portion is a second unidirectional tooth arranged to protrude from the handle.

Optionally, the first engaging portion is a first elastic piece, with one end of the first elastic piece being connected on the trolley, while the other end of the first elastic piece being configured to be in locking cooperation with the first unidirectional tooth when moving in the first direction, and to be in slidable cooperation with the first unidirectional tooth when moving in the second direction; and the second engaging portion is a second elastic piece, with one end of the second elastic piece being connected on the trolley, while the other end of the second elastic piece being configured to be in locking cooperation with the second unidirectional tooth when moving in the first direction, and to be in slidable cooperation with the second unidirectional tooth when moving in the second direction.

The beneficial effects of the channel device for surgery and the trigger structure according to the embodiments of the present disclosure comprises, for example:

in the channel device for surgery, the binding cord is flexible and can be arbitrarily wound around the metal net; the hardness of the binding wire is higher than that of the binding cord, and the binding wire can tighten up the binding cord after passing through the binding cord, and tighten up the metal net through the binding cord, hereby realizing the compression of the metal net; and after that the binding wire is pulled away from the binding cord, the binding cord disperses rapidly and the metal net returns to its original shape, hereby forming a surgical channel. When assembling the channel device for surgery, the binding cord is flexible and can relatively easily pass through the metal net, meanwhile, the binding wire is only required to pass through the binding cord, thus, the assembly is simple and the assembling efficiency is improved; and during actual surgical operations, it is only required to draw the binding wire out of the binding cord, hereby significantly improving the operational efficiency of surgery.

As for the trigger structure, different first locking portions on the trigger are enabled, by sliding the trigger, to be in cooperation with the first engaging portion, so as to drive the trolley to slide intermittently, such that the second engaging portion of the trolley cooperates with different second locking portions, hereby realizing the locking of the trolley in different positions on the handle, wherein it is only required during the whole course to continuously operate the trigger, hereby realizing the fixing of the trolley in different positions on the handle along the sliding direction, thus, the operation is simple and the operational efficiency is improved.

BRIEF DESCRIPTION OF THE DRAWINGS

In order to more clearly describe the technical solutions of the embodiments of the present disclosure, the drawings to be used in the embodiments will be simply presented below; and it shall be understood that the following drawings merely show certain embodiments of the present disclosure, and thus should not be deemed as limiting the scope thereof, and for a person ordinarily skilled in the art, further relevant drawings could be obtained according to these drawings without inventive efforts.

REFERENCE SIGNS

Figure 1:
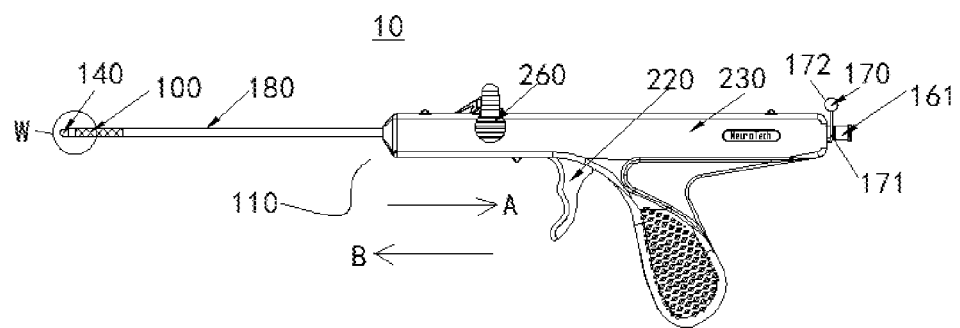
FIG. 1 is a schematic view showing the overall structure of a channel device for surgery provided in an embodiment of the present disclosure.

10—channel device for surgery; 100—metal net; 101—mesh; 110—conveyor; 111—channel; 120—binding cord; 121—loop hole; 130—binding wire; 140—puncture head; 141—first hole; 142—injection hole; 150—fixing block; 151—limit hole; 152—assembly hole; 160—supporting tube; 161—Luer taper; 170—snap ring; 171—semicircular ring; 172—toggle handle; 180—outer tube; 20—trigger structure; 210—trolley; 211—first engaging portion; 212—second engaging portion; 220—trigger; 221—first locking portion; 230—handle; 231—second locking portion; 260—lock catch; 250—spring; 300—retractor device; 310—outer sheath; 320—inner core; and 330—buckle.

Detailed Description of the Embodiments

In order to make the objects, the technical solutions and the advantages of the embodiments of the present disclosure dearer, the technical solutions of the embodiments of the present disclosure will be dearly and comprehensively described below with reference to the attached figures in the embodiments of the present disclosure. Clearly, the described embodiments are merely some of the embodiments of the present disclosure, but not all the embodiments. Generally, the assemblies of the embodiments of the present disclosure that are described and shown here in the figures may be arranged and designed according to various configurations.

Thus, the following detailed description of the embodiments of the present disclosure that are provided in the figures merely represents selected embodiments of the present disclosure, rather than being intended to limit the scope of the present disclosure for which protection is sought. Any other embodiments, obtained by a person ordinarily skilled in the art without inventive efforts based on the embodiments in the present disclosure, shall fall within the scope of protection of the present disclosure.

It shall be noted that similar reference signs and letters represent similar items in the following figures, thus, once a certain item is defined in one figure, no further definition and explanation of this item is necessary in the subsequent figures.

In the description of the present disclosure, it shall be clarified that orientation or position relationships indicated by terms such as "upper", "lower", "inner", or "outer", if used, are orientation or position relationships shown based on the figures, or orientation or position relationships in which the product of this disclosure is conventionally placed during use, merely for the purpose of facilitating the description of the present disclosure and for simplifying the description, rather than indicating or implying that a specified device or element must have a specific orientation, and be constructed and operated in a certain orientation, and therefore cannot be construed as limiting the present disclosure.

In addition, terms such as "first" or "second", if used, are used merely for purpose of differentiated description, and cannot be construed as indicating or implying to have importance in relativity.

It shall be clarified that the features in the embodiments of the present disclosure may be combined with each other without conflicts.

Existing channel devices have the problem of low operational efficiency. It is discovered by the inventors in research that existing metal nets for forming a surgical channel cannot be released quickly enough; and it is discovered in further research that methods for compressing a metal net are relatively complicated, causing that the metal net cannot be released quickly, and accordingly affecting the operational efficiency. The channel device for surgery and the trigger structure provided in the present embodiment can improve the problem mentioned above.

Hereinafter, the channel device for surgery provided in the present embodiment will be described in detail with reference to FIGS. 1 to 8.

Referring to FIG. 1, the present embodiment provides a channel device for surgery 10, comprising: a retractor, including a metal net 100 configured to form a surgical channel 111; a conveyor 110, wherein the distal end of the conveyor 110 has an openable channel 111 configured for placing the metal net 100; a binding cord 120, configured to be wound around the metal net 100; and a binding wire 130, configured to pass through the binding cord 120 and tighten up the binding cord 120, so as to compress the metal net 100, or configured to be pulled away from the binding cord 120, so as to loosen the binding cord 120 and the metal net 100.

The following contents shall be clarified. A person skilled in the art could understand that in the context, during the application of the channel device for surgery 10, the front end of the conveyor 110 is configured to extend into brain tissue, so as to deliver the front end of the retractor into the brain tissue, while the rear end of the conveyor 110 is operated by a doctor. Thus, the part of each component close to the front end of the conveyor 110 is correspondingly marked as distal end of this component, while the part of the component close to the rear end of the conveyor 110 is correspondingly marked as proximal end of this component. In the above, the front end of the conveyor 110 is the distal end of the conveyor 110, and the rear end of the conveyor 110 is the proximal end of the conveyor 110.

Referring further to FIG. 1, the retractor includes a metal net 100, which is woven from a memory alloy material. The retractor can be compressed to a very small diameter, then delivered into the brain tissue, and return to the originally designed shape after being released relying on its own elasticity and memory performance, hereby strutting the brain tissue and forming a surgical channel 111, which is necessary for microscopic/endoscopic therapy, such that the range of applying microscopic/endoscopic procedures is greatly improved and trauma to the brain tissue is reduced. The process of incising the brain tissue is reduced by compressing the retractor to a very small diameter and inserting the same into the brain tissue. In the present embodiment, the retractor having returned to its original shape is in the shape of a hollow cylinder. The retractor further includes a transparent film layer, which covers the external surface of the metal net 100 and is configured to increase the smoothness of the external surface of the metal net 100, so as to reduce trauma to the brain tissue.

Referring further to FIG. 1, the conveyor 110 is configured to deliver and insert the retractor compressed to a very small diameter into the brain tissue. The channel 111 can be opened, and the metal net 100 is placed in the channel 111; and after that the channel 111 is opened, the metal net 100 is completely exposed and then released, hereby forming a surgical channel 111. In the present embodiment, the metal net 100 is in the compressed state when being located in the channel 111, and after that the channel 111 is opened, the metal net 100 is released and then returns to its original shape.

Referring further to FIG. 1, in the present embodiment, the binding cord 120 can be wound around the metal net 100, and the metal net 100 can be tightened by straining the binding cord 120. The binding wire 130 tightens the binding cord 120 on the binding wire 130 by passing through the binding cord 120. In the present embodiment, the compression of the metal net 100 can be realized by connecting multiple points on the metal net 100 with one single point on the binding wire 130 via the binding cord 120 and tightening the plurality of points to one single point.

Figure 3:
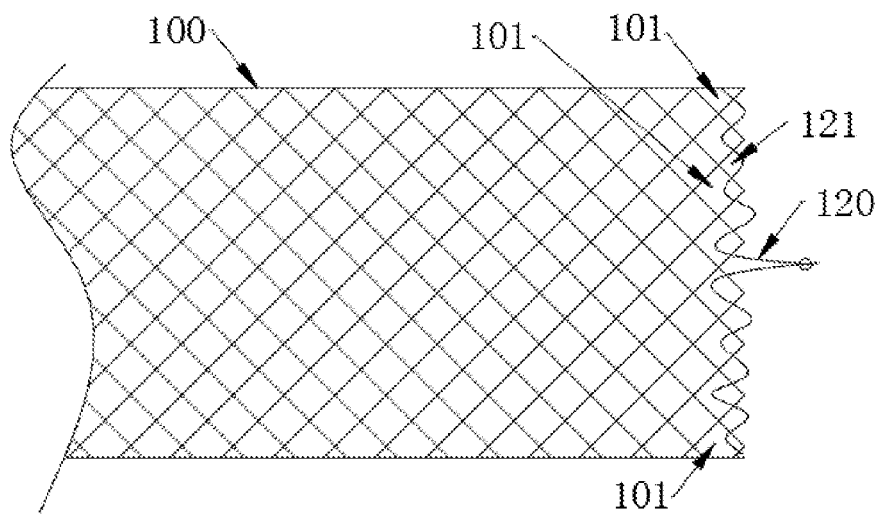
FIG. 3 is a structural schematic view of a retractor provided in an embodiment of the present disclosure.
Figure 4:
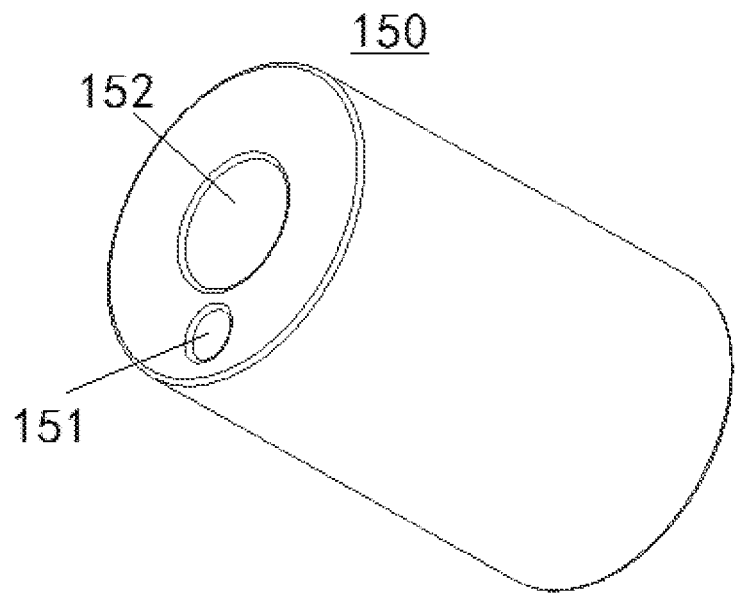
FIG. 4 is a structural schematic view of a fixing block provided in an embodiment of the present disclosure.

Specifically, referring to FIG. 3, the binding cord 120 is configured to sequentially pass through a plurality of meshes 101 at the distal end of the metal net 100, so as to form a plurality of loop holes 121 with the metal net 100, with the plurality of loop holes being distributed along a circumferential direction of the metal net 100. Specifically, the distal end of the metal net 100 has a plurality of meshes 101 sequentially distributed along the circumferential direction, and one end of the binding cord 120 penetrates through one of the meshes 101 and exits from an adjacent mesh 101, wherein the threading directions of the binding cord 120 through two adjacent meshes 101 are opposite to each other, and a loop hole 121 is formed accordingly by the binding cord 120 penetrating through two adjacent meshes 101. In the above, in the present embodiment, both ends of the binding cord 120 are connected from end to end. In other embodiments, both ends of the binding cord 120 may be connected to the metal net 100.

In the above, a nylon cord or other flexible cords may be used as the binding cord 120.

Referring further to FIG. 3, the binding wire 130 is configured to sequentially pass through the plurality of loop holes 121 and to tighten up the binding cord 120 when in a straightened state. After that the distal end of the binding wire 130 sequentially passes through the plurality of loop holes 121 along the circumferential direction, the binding wire 130 is straightened, and binding cords 120 having passed through two adjacent meshes 101 are both sleeved on the binding wire 130 and gathered together, hereby realizing the compression of the metal net 100.

By utilizing the flexible feature of the binding cord 120, the metal net 100 can be tightened up on the binding wire 130 in the straightened state, and the binding cord 120 can be easily wound around the metal net 100, thus, the assembly is simple. By withdrawing the binding wire 130 out of the binding cord 120, the binding cord 120 and the metal net 100 can be loosened, thus, the operation is simple.

Figure 2:
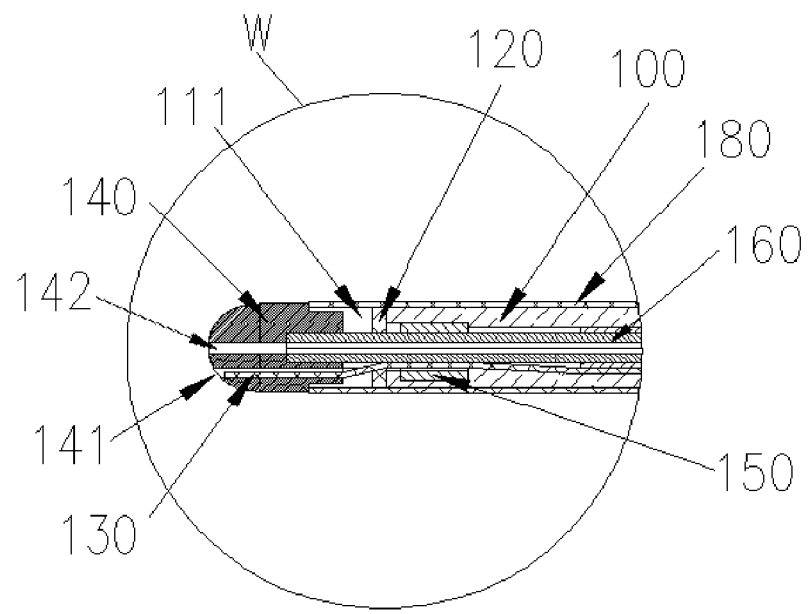
FIG. 2 is a partially enlarged view of W in FIG. 1.

Referring to FIG. 1 again and with reference to FIG. 2, in the present embodiment, the conveyor 110 includes a puncture head 140, provided with a first hole 141 in communication with the channel 111, when the binding wire 130 is in the straightened state, the distal end of the binding wire 130 is accommodated in the first hole 141, and the proximal end of the binding wire 130 extends in a direction away from the first hole 141, so as to be configured to move under the action of an external force, and accordingly pull the binding wire 130 away from the binding cord 120.

The puncture head 140 is configured to puncture the brain tissue during surgery. The description is made on the basis of the relative positions in FIG. 1, the puncture head 140 is arranged at the leftmost end of the conveyor 110, the puncture head 140 and the channel 111 are successively arranged from left to right, and the right end of the first hole 141 is in communication with the channel 111. The distal end of the binding wire 130 passes through the binding cord 120 and then extends into the first hole 141. The first hole 141 has the effects of supporting and limiting the binding wire 130, to prevent the binding wire 130 from moving arbitrarily and to keep the binding cord 120 tightened up on the binding wire 130, hereby keeping the compressed state of the metal net 100; meanwhile, it has the effect of limiting the position of the metal net 100 to prevent the metal net 100 from moving towards the proximal end of the channel 111. In the present embodiment, the first hole 141 is provided on a lateral portion of the puncture head 140, and the position of the first hole 141 is designed according to the position of the binding wire 130 at the distal end when being in the straightened state. The left end of the first hole 141 runs through the puncture head 140, or the left end of the first hole 141 is closed.

Referring further to FIG. 2, in the present embodiment, the conveyor 110 further includes a fixing block 150, which is fixed in the channel 111 and provided with a limit hole 151; and the binding wire 130 is configured to pass movably through the limit hole 151 and is positionally limited by means of the fixing block 150. Specifically, both ends of the limit hole 151 are perforative. There is a gap between the fixing block 150 and the puncture head 140, and the distal end of the metal net 100 is located in the gap; and after passing through the limit hole 151, the distal end of the binding wire 130 then passes through the binding cord 120, and extends into the first hole 141 after being straightened. The limit hole 151 has a position limiting effect on the binding wire 130, such that the binding wire 130 can more easily keep the straightened state, and the influence of other components on the straightened state of the binding wire 130 is reduced.

Referring further to FIG. 2, in the present embodiment, the fixing block 150 is arranged at the distal end of the channel 111, and is located on the inner side of the metal net 100, so as to be configured to prevent the metal net 100 from moving towards the proximal end of the channel 111. The metal net 100 is sleeved over the outer periphery of the fixing block 150; after that the distal end of the metal net 100 is compressed, the metal net 100 is obstructed by the fixing block 150 and thus cannot move towards the proximal end of the channel 111, and the metal net 100 is accordingly further limited at the distal end of the channel 111.

Referring further to FIG. 2, in the present embodiment, the puncture head 140 is provided with an injection hole 142 communicating the channel 111 and the exterior; the conveyor 110 further includes a supporting tube 160 and a Luer taper 161, wherein the supporting tube 160 is arranged within the channel 111, and the distal end of the supporting tube 160 is in connection with the puncture head 140 and is in communication with the injection hole 142; and the Luer taper 161 is in communication with the proximal end of the supporting tube 160, so as to be configured for liquid injection. Further, the Luer taper 161 is in communication with the proximal end of the supporting tube 160.

The Luer taper 161 is a standardized non-permeable trace connector, and connection is realized through a male Luer taper 161 and a matching female Luer taper 161. The Luer taper 161 is configured to inject liquid, which enters the supporting tube 160 and then is ejected from the injection hole 142, or is configured to irrigate or suck up the cerebral effusion during the process of inserting the channel device for surgery 10 into the brain tissue.

Specifically, referring to FIG. 1, the end portion of the puncture head 140 is in oval shape. It helps to push blood vessels aside during the insertion process without causing the blood vessel to be severed. The process of strutting the brain tissue by the retractor indicates flexible strutting in a peripheral direction, the force is applied in the peripheral direction, in which the force bearing area in this case is greater than that of the situation where the brain tissue is pushed towards both sides by two brain spatulas, thus, it would not cause local overpressure of the brain tissue, which is usually caused by the use of brain spatulas.

In the above, the injection hole 142 is provided in the middle of the puncture head 140, and both ends of the injection hole 142 respectively penetrate both ends of the puncture head 140. Specifically, the distal end of the supporting tube 160 is inserted in the puncture head 140 and is in communication with the injection hole 142.

In the above, referring to FIG. 1, the fixing block 150 is fixed on the supporting tube 160. Specifically, with reference to FIG. 4, the fixing block 150 is provided with an assembly hole 152, the limit hole 151 and the assembly hole 152 are arranged with an interval therebetween, and the supporting tube 160 passes through the assembly hole 152 and is fixed.

Referring further to FIG. 2, in the present embodiment, the channel 111 device for surgery further comprises an outer tube 180, the outer tube 180 is slidably sleeved over the outer side of the supporting tube 160, and the channel 111 is formed between the internal wall of the outer tube 180 and the external wall of the supporting tube 160. The circular tubular channel 111 achieves a clear visual field and greatly improves the difficulty and control of the surgical procedure, making this surgery convenient and easy to promote, and can be combined with stereotaxis or computer navigation to achieve the effect of precise positioning of the operative region.

Specifically, the distal end of the outer tube 180 is in contact with the puncture head 140, to seal the channel 111. The metal net 100 is sleeved between the supporting tube 160 and the outer tube 180, and the distal end of the metal net 100 is tightened on the supporting tube 160 after compression. When the outer tube 180 slides relative to the supporting tube 160, the channel 111 is opened and the metal net 100 is exposed; the metal net 100 is released under the action of elastic restoring force and then unfolded; and after the binding wire 130 is removed, the distal end of the metal net 100 is also released and unfolded.

Referring to FIG. 1 again, in the present embodiment, the conveyor 110 further includes a snap ring 170, which is in connection with the binding wire 130, so as to be configured to pull the binding wire 130 away from the binding cord 120 under the action of an external force. After that the channel 111 is opened, the snap ring 170 is pulled by the external force, to pull the binding wire 130 away from the binding cord 120, so as to release the metal net 100. Referring further to FIG. 1, in the present embodiment, the conveyor 110 further includes a damping portion, and the snap ring 170 is configured to be clamped with or disengaged from the damping portion, when the snap ring 170 is disengaged from the damping portion, the snap ring 170 is configured to pull the binding wire 130 away from the binding cord 120 under the action of an external force. The fixing of the snap ring 170 is realized by clamping the same on the clamping portion, and after that the channel 111 is opened, the snap ring 170 is removed, and the snap ring 170 and the binding wire 130 are then be pulled. Referring further to FIG. 1, in the present embodiment, the clamping portion is column-shaped; and the snap ring 170 includes a semicircular ring 171 and a toggle handle 172 which are in connection with each other, wherein the semicircular ring 171 is configured to be clamped with or disengaged from the external wall of the damping portion. The damping of the semicircular ring 171 with the damping portion and its disengagement from the damping portion are realized through the toggle handle 172. Specifically, the shape of a circular ring is adopted for the toggle handle 172.

Referring further to FIG. 1, in the present embodiment, the Luer taper 161 partially forms the clamping portion, and the semicircular ring 171 is configured to be damped with or disengaged from the external wall of the Luer taper 161. When the snap ring 170 is disengaged from the Luer taper 161, the snap ring 170 is configured to move under the action of an external force, so as to pull the binding wire 130 away from the binding cord 120.

Specifically, the proximal end of the binding wire 130 is in connection with the snap ring 170.

The snap ring 170 includes a first connecting section extending in the axial direction of the Luer taper 161, one end of the first connecting section is in connection with the binding wire 130, and the other end of the first connecting section is in connection with one end of the semicircular ring 171, which extends along the circumferential direction of the Luer taper 161. The snap ring 170 further includes a second connecting section, and the semicircular ring 171 and the toggle handle 172 are in connection with each other through the second connecting section, wherein the second connecting section and the semicircular ring 171 are located in the same plane, and the second connecting section is arranged along the diameter direction of the semicircular ring 171. The second connecting section is perpendicular to the first connecting section.

When being assembled, the end of the first connecting section away from the semicircular ring 171 is connected to the binding wire 130, and the semicircular ring 171 is clamped on the Luer taper 161. When the binding wire 130 needs to be pulled out, it is required to hold the toggle handle 172 to drive the semicircular ring 171 to rotate, such that the semicircular ring 171 falls off the Luer taper 161, and accordingly, the snap ring 170 can be held to pull the binding wire 130 outwards, hereby pulling the binding wire 130 away from the binding cord 120 and realizing the release of the binding cord 120.

Referring to FIGS. 5-8, an embodiment of the present disclosure further provides a trigger structure 20, comprising: a trolley 210, a trigger 220, and a handle 230; the trigger 220 and the trolley 210 are commonly slidably arranged on the handle 230; the trolley 210 is provided with a first engaging portion 211 and a second engaging portion 212; the trigger 220 is provided with a first locking portion 221, and there is a plurality of first locking portions 221; the handle 230 is provided with a second locking portion 231, and there is a plurality of second locking portions 231; and different first locking portions 221 are configured to cooperate with the first engaging portion 211, so as to drive the trolley 210 to slide intermittently relative to the handle 230, such that the second engaging portion 212 cooperates with different second locking portions 231, hereby locking the sliding trolley 210 in different positions on the handle 230.

Different first locking portions 221 on the trigger 220 are enabled, by sliding the trigger 220, to be in cooperation with the first engaging portion 211, so as to drive the trolley 210 to slide intermittently, such that the second engaging portion 212 of the trolley 210 cooperates with different second locking portions 231, hereby realizing the locking of the trolley 210 in different positions on the handle 230, wherein it is only required during the whole course to continuously operate the trigger 220, hereby realizing the fixing of the trolley 210 in different positions on the handle 230 along the sliding direction, thus, the operation is simple and the operational efficiency is improved.

Figure 5:
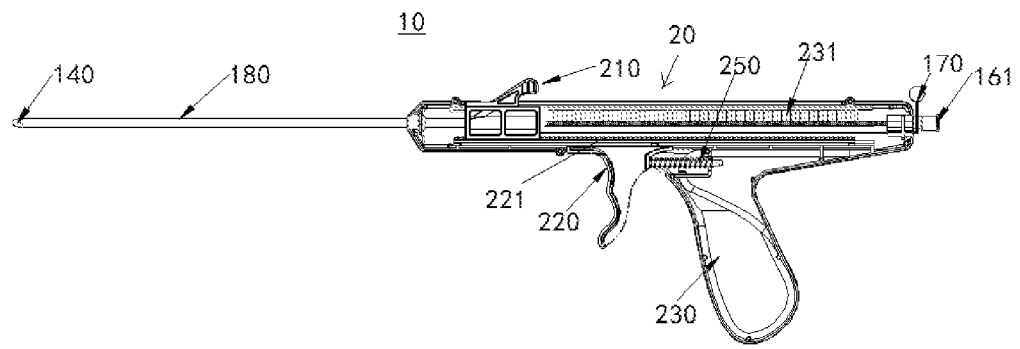
FIG. 5 is a partial sectional view of a channel device for surgery provided in an embodiment of the present disclosure.

Referring further to FIG. 5, the first locking portion 221 is configured to be in locking cooperation with the first engaging portion 211, when the trigger 220 slides relative to the handle 230 in a first direction, such that the trigger 220 pushes the trolley 210 to slide in the first direction; and the first locking portion 221 is configured to be in slidable cooperation with the first engaging portion 211, when the trigger 220 slides relative to the handle 230 in a second direction, wherein the trolley 210 is fixed relative to the handle 230, when the first locking portion 221 is in slidable cooperation with the first engaging portion 211, wherein the first direction is opposite to the second direction.

It shall be clarified that the "first direction" is the direction indicated by arrow A in FIG. 1, and the "second direction" is the direction indicated by arrow B in FIG. 1.

Specifically, the trigger 220 moves in the first direction, and at this moment, the first locking portion 221 can be in locking cooperation with the first engaging portion 211, and when the trigger 220 moves in the first direction, the trolley 210 is driven to move synchronously in the first direction. During the moving process of the trolley 210 in the first direction, the second engaging portion 212 can continuously cooperate with different second locking portions 231, so as to lock the trolley 210 in different positions. When the trigger 220 moves in the second direction, the first locking portion 221 is in slidable cooperation with first engaging portion 211, and the movement of the trigger 220 in the second direction would not affect the movement of the trolley 210, and the trolley 210 is still locked on the handle 230. Therefore, the continuous reciprocating movement of the trigger 220 in the first direction and the second direction can continuously push the trolley 210 to continuously move in the first direction.

Referring to FIG. 5 again, in the present embodiment, the trigger structure 20 further includes a reset member, wherein the reset member is connected between the trigger 220 and the handle 230, such that the trigger 220 has a tendency to slide relative to the handle 230 in the second direction. Specifically, a spring 250 is used as the reset member, wherein one end of the spring 250 is in connection with the handle 230, while the other end of the spring 250 is in connection with the trigger 220.

The trigger 220 is driven by external force to move in the first direction, which accordingly drives the trolley 210 to move in the first direction, and the removal of the external force does not interfere with the fixing of the trolley 210 relative to the handle 230. After the removal of the external force, the trigger 220 moves in the second direction under the action of the reset member, and the trigger 220 is reset, then an external force is applied again to push the trigger 220 to move in the first direction, which in turn drives the trolley 210 to move another distance further in the first direction.

By repeatedly pushing the trigger 220 and removing the external force in such a manner, the trolley 210 is pushed to continuously move in the second direction during the reciprocating movement of the trigger 220 in the first direction and the second direction.

Figure 6:
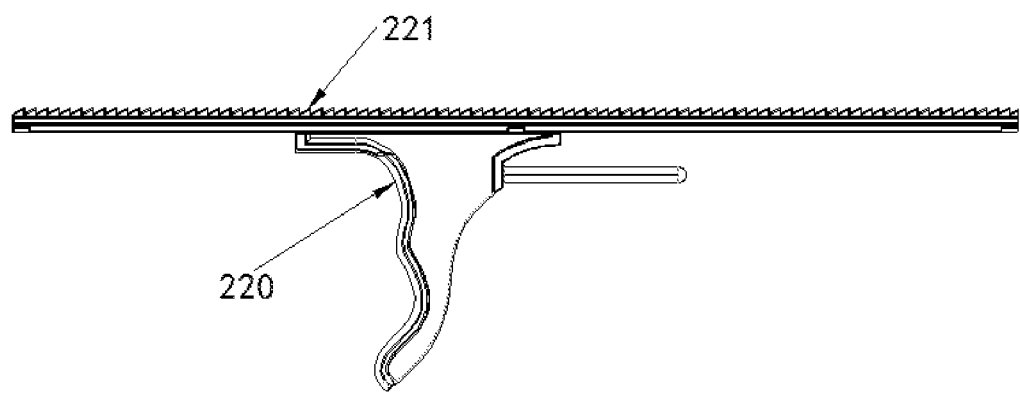
FIG. 6 is a structural schematic view of a trigger provided in an embodiment of the present disclosure.

Referring to FIG. 5 again and with reference to FIG. 6, the first locking portion 221 is a first unidirectional tooth arranged to protrude from the trigger 220; and the second locking portion 231 is a second unidirectional tooth arranged to protrude from the handle 230.

When moving in the first direction, the first unidirectional tooth of the trigger 220 is locked with the first engaging portion 211, so as to drive the first engaging portion 211 to move. When moving in the second direction, the first unidirectional tooth is in slidable cooperation with the first engaging portion 211, and is not interfered by the first engaging portion 211, and vice versa.

When moving in the first direction, the second engaging portion 212 of the trolley 210 is in slidable cooperation with the second unidirectional tooth, thus, the trolley 210 can continuously move in the first direction. The second engaging portion 212 of the trolley 210 is not movable in the second direction and is locked on the second unidirectional tooth.

Figure 7:
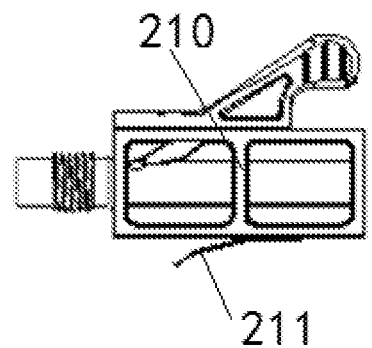
FIG. 7 is a structural schematic view showing a trolley in a first viewing angle provided in an embodiment of the present disclosure.

Referring to FIG. 7, in the present embodiment, the first engaging portion 211 is a first elastic piece, with one end of the first elastic piece being connected on the trolley 210, while the other end of the first elastic piece being configured to be in locking cooperation with the first unidirectional tooth when moving in the first direction, and to be in slidable cooperation with the first unidirectional tooth when moving in the second direction.

Figure 8:
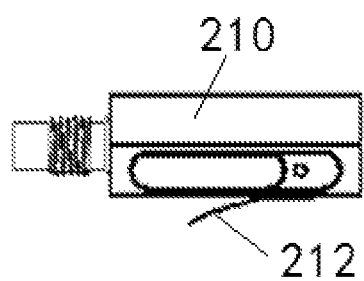
FIG. 8 is a structural schematic view showing a trolley in a second viewing angle provided in an embodiment of the present disclosure.

Referring to FIG. 8, in the present embodiment, the second engaging portion 212 is a second elastic piece, with one end of the second elastic piece being connected on the trolley 210, while the other end of the second elastic piece being configured to be in locking cooperation with the second unidirectional tooth when moving in the first direction, and to be in slidable cooperation with the second unidirectional tooth when moving in the second direction.

Specifically, with reference to FIG. 5, the description is made on the basis of the relative positions in FIG. 5, the trolley 210 and the trigger 220 are both arranged on the handle 230, and the trolley 210 is arranged above the trigger 220. The first elastic piece is arranged at the bottom of the trolley 210, wherein the proximal end of the first elastic piece is connected to the bottom of the trolley 210, and the distal end of the first elastic piece is arranged at an angle with the bottom of the trolley 210; and the first unidirectional tooth is arranged in the first direction, and arranged at the top of the trigger 220, wherein the first unidirectional tooth is a beveled tooth and is inclined towards the upper right.

The distal end of the first elastic piece is in cooperation with the first unidirectional tooth, the first elastic piece is slidable relative to the first unidirectional tooth in the first direction, while in the second direction, the first elastic piece is locked with the first unidirectional tooth and is not movable in the second direction.

Further, the second elastic piece is arranged on a lateral portion of the trolley 210, the proximal end of the second elastic piece is connected to the lateral portion of the trolley 210, and the distal end of the second elastic piece is arranged at an angle with the lateral portion of the trolley 210; and the second unidirectional tooth is arranged in the handle 230 along the first direction and corresponds to the lateral portion of the trolley 210, wherein the second unidirectional tooth is also a beveled tooth and is inclined towards the upper right. The distal end of the second elastic piece is in cooperation with the second unidirectional tooth, the second elastic tooth is slidable relative to the second unidirectional tooth in the first direction, while in the second direction, the second elastic piece is locked with the second unidirectional tooth and is not movable in the second direction.

Referring to FIGS. 1 and 5 again, the conveyor 110 further includes a lock catch 260; the handle 230 is provided with a slideway, on which the trolley 210 is slidably arranged; the handle 230 is provided with two jack sockets and the slideway passes between the two jack sockets; and the trolley 210 is provided with a limit grip. The lock catch 260 is detachably clamped with the two jack sockets, wherein when the lock catch 260 is clamped with the two jack sockets, the lock catch 260 can abut against the limit grip to prevent the trolley 210 from moving towards the distal end of the conveyor 110, and when the lock catch 260 is disengaged from the jack sockets, the trolley 210 can move along the distal end of the conveyor 110. Therefore, before operating the trigger 220 to drive the trolley 210 to move in the first direction, the lock catch 260 needs to be pulled out from the jack sockets. The lock catch 260 is mainly used to prevent misoperation.

Specifically, the lock catch 260 includes a first locking bar and a second locking bar, wherein the first locking bar and second locking bar are arranged to be perpendicular to each other, one end of the second locking bar is connected to the middle of the first locking bar, and the second locking bar is configured to cooperate with the jack sockets. In actual operation, an operator can insert the second locking bar into the jack sockets or disengage the same from the jack sockets just by holding the first locking bar.

It shall be clarified that the term "perpendicular" in the context does not require that the included angle between two components must be 90°, but can have slight deviation, for example, two components can be deemed to be perpendicular to each other when having an included angle in the range of 88°-90°. For example, the included angle between the first locking bar and the second locking bar may also be 88°, 89°, and so on.

In addition, in the channel device for surgery 10, the trolley 210 is in connection with the outer tube 180, and when the trolley 210 is sliding relative to the handle 230, the outer tube 180 is driven to move, so as to open the channel 111. Specifically, the proximal end of the outer tube 180 is in connection with the trolley 210. Further, the proximal end of the outer tube 180 is provided with an internally threaded section, while the trolley 210 is provided with an externally threaded section, and the internally threaded section and the externally threaded section are in threaded connection with each other. By driving the trigger 220 to move, the trigger 220 continuously drives the trolley 210 to move in the first direction, which drives the outer tube 180 to move in the first direction, hereby opening the channel 111 and releasing the metal net 100 to form a surgical channel 111.

In the present embodiment, since the retractor is relatively soft, the direction of the channel 111 needs to be adjusted during the surgery, and the direction of the retractor cannot be directly turned. In the present embodiment, the direction of the surgical channel 111 is adjusted through a retractor device 300, that is, the surgical channel 111 established by the metal net 100 is adjusted, which is realized specifically by adjusting the direction of the retractor. Specifically, the retractor device 300 is inserted into the metal net 100 for adjusting the direction.

Figure 9:
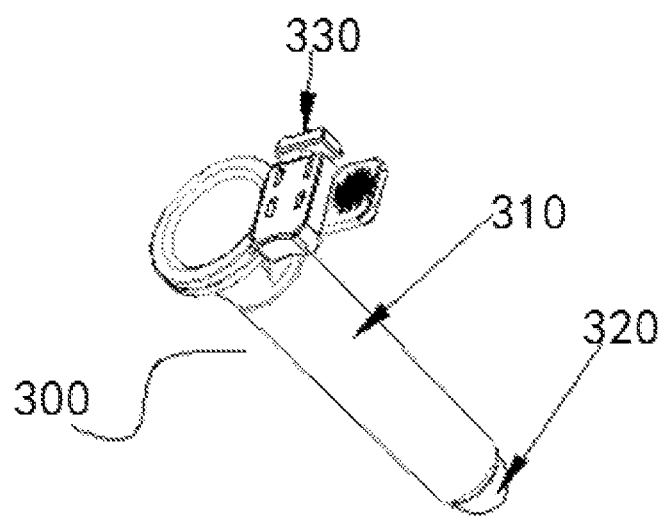
FIG. 9 is a structural schematic view of a retractor device provided in an embodiment of the present disclosure.
Figure 10:
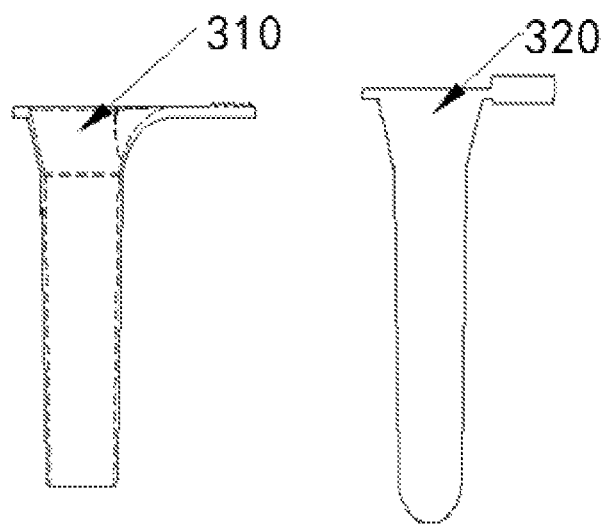
FIG. 10 is a structural schematic view showing an outer sheath and an inner core in the retractor device provided in an embodiment of the present disclosure.

Referring to FIGS. 9 and 10, the retractor device 300 provided in the present embodiment comprises a tubular outer sheath 310 and an inner core 320 having a round head at one end, wherein the outer sheath 310 and the inner core 320 are movably sleeved and are in detachable connection with each other, wherein the round head of the inner core 320 extends beyond the outer sheath 310, and the outer sheath 310 is further provided with a connection structure configured to connect with external equipment. Herein, the outer sheath 310 and the inner core 320 are locked via a buckle 330. In actual use, the inner core 320 is inserted in the outer sheath 310 and is in fixed connection therewith via the buckle 330, when inserting the outer sheath 310 together with the inner core 320 into the metal net 100, the round head of the inner core 320 is configured to contact the brain tissue and avoid trauma to the brain tissue; the inner core 320 is then removed, and the outer sheath 310 can be rotated according to the direction to be reached after adjustment; and after the direction adjustment is completed, the outer sheath 310 is fixedly connected to external equipment via the connection structure, hereby finishing the adjustment to the surgical channel 111 formed by the metal net 100.

Further, the outer sheath 310 and the inner core 320 are made of PC or a similar transparent hard material, wherein transparent materials allow convenient observation of situation of surrounding brain tissue.

According to the channel device for surgery 10 provided in this embodiment, the use process of the channel device for surgery 10 is as follows:

Step 1: removing the lock catch 260;

Step 2: pulling the trigger 220, wherein the outer tube 180 retracts now towards the proximal end of the conveyor 110, the trigger 220 is repeatedly pulled till the retractor completely projects out of the outer tube 180, and at this moment, the proximal end of the retractor opens, while the distal end of the retractor is fixed between the puncture head 140 and the fixing block 150 because of the binding of the binding cord and the binding wire 130.

Step 3: rotating the snap ring 170 to disengage the same from the Luer taper 161, then retracting the snap ring 170 backwards, and drawing the binding wire 130 out of the puncture head 140, the binding cord 120 and the fixing block 150, such that the distal end of the retractor is released, and the retractor is now not in connection with the supporting tube 160; and removing the conveyor 110, wherein the retractor returns to the cylindrical shape under the action of its own elasticity and is separated from the supporting tube 160, and the retractor will form an channel 111 required for the surgery if the conveyor 110 is removed now.

According to the channel device for surgery 10 provided in this embodiment, the method steps for performing surgery using the channel device for surgery 10 are as follows (taking cerebral hemorrhage as example):

1. Labelling a mark on the head of a patient with cerebral hemorrhage after skin preparation, and performing head CT or MRI examination;
2. Inputting the examination data into the computer workstation;
3. Confirming the scalp incision site;
4. Routinely sterilizing and draping after general anesthesia;
5. Cutting the scalp, wherein straight incision can be used;
6. Performing abrasive drilling to form a free bone flap with a diameter of 3 cm;
7. Cutting the cerebral dura mater;

8. Inserting the puncture head 140 of this product and the front end part of the outer tube 180 connected thereto in the cortical avascular area under the guidance of a navigation bar; removing the lock catch 260 after accurately entering the hematoma cavity, and pulling the trigger 220, such that the outer tube 180 is slowly disengaged from the retractor, wherein initially, the binding cord 120 at the front end of the retractor is fixed on the puncture head 140 through the binding wire 130. During the process of disengaging the outer tube 180 slowly from the retractor, the rear part of the retractor slowly expands to form a rear end channel 111; after complete release of the retractor (i.e. complete separation from the outer tube 180), the snap ring 170 at the rear end of the handle 230 is rotated, such that it is loosened from the Luer taper 161; the snap ring 170 is then retracted, such that the binding wire 130 at the front end of the retractor is separated from the metal net 100, and the distal end of the retractor spreads out now, until the whole retractor is completely released. The conveyor 110 is removed to form a surgical passage. Microscopic/endoscopic removal of hematoma is performed through this passage, and after satisfying hemostasis, the retractor is gently pinched (the distal end of the metal net 100 enters the brain tissue transported by the conveyor 110, and the proximal end of the metal net 100 is located outside of the brain tissue, and the now gently pinched part is the proximal end of the metal net 100) and can be pulled out after shrinkage, and surgicel is applied in the puncture passage under the microscope/endoscope;

9. Tightly suturing the cerebral dura mater;
10. Fixing with a bone flap reduction titanium bar; and
11. Suturing respective layers of the scalp.

The channel device for surgery 10 provided in this embodiment has at least the following advantages.

The compression of the metal net 100 is realized by utilizing a binding cord 120 and a binding wire 130, the structure is simple and reliable, and the assembly is simple; during operation, it is only required to pull the binding wire 130 away from the binding cord 120, for realizing the release of the metal net 100, thus, the operation is simple, the surgical efficiency is improved, and the surgical risk is reduced.

The opening of the channel 111 is realized by utilizing the trigger structure 20, and the retraction of the outer tube can be realized by repeatedly operating the trigger 220, thus, the operation is convenient; meanwhile, the trigger 220 only requires single-hand operation, which further simplifies the operation and improves the operational efficiency.

When the lock catch 260 is inserted on the handle 230, the trigger 220 and the trolley 210 are not movable, and for normal operation, it is required to firstly remove the loch catch 260 and then realize the retraction of the outer tube 180 by pulling the trigger 220, thus, the lock catch 260 has the function of preventing misoperation of the trigger 220, causing retraction of the outer tube 180 and accidental release of the metal net 100.

The above mentioned are merely specific embodiments of the present disclosure. However, the scope of protection of the present disclosure is not limited thereto, and any technician familiar with this technical field can readily think of variations or substitutions within the technical scope disclosed in the present disclosure, and these variations and substitutions shall be covered in the scope of protection of the present disclosure. Thus, the scope of protection of the present disclosure shall be defined according to the scope of protection of the claims.

The invention claimed is:

1. A channel device for surgery, comprising:
   a retractor, wherein the retractor comprises a metal net configured to form a surgical channel;
   a conveyor, wherein a distal end of the conveyor has an openable channel configured for the metal net to be placed; and
   a binding cord and a binding wire, wherein the binding cord is configured to be wound around the metal net, and the binding wire is configured to pass through the binding cord and tighten up the binding cord, so as to compress the metal net, or the binding wire is configured to be pulled away from the binding cord, so as to loosen the binding cord and the metal net.

2. The channel device for surgery according to claim 1, wherein the binding cord is configured to sequentially pass through a plurality of meshes at a distal end of the metal net, so as to form a plurality of loop holes with the metal net, with the plurality of loop holes being distributed along a circumferential direction of the metal net.

3. The channel device for surgery according to claim 2, wherein the binding wire is configured to sequentially pass through the plurality of loop holes and to tighten up the binding cord when the binding wire is in a straightened state.

4. The channel device for surgery according to claim 3, wherein the conveyor comprises a puncture head, wherein the puncture head is provided with a first hole in communication with the surgical channel, and
   when the binding wire is in the straightened state, a distal end of the binding wire is accommodated in the first hole, and a proximal end of the binding wire extends in a direction away from the first hole, so as to be configured to move under an action of an external force, and accordingly, the binding wire is pulled away from the binding cord.

5. The channel device for surgery according to claim 4, wherein the conveyor further comprises a fixing block, wherein the fixing block is fixed in the surgical channel and provided with a limit hole; and
   the binding wire is configured to pass movably through the limit hole and is positionally limited by means of the fixing block.

6. The channel device for surgery according to claim 5, wherein the fixing block is arranged at a distal end of the surgical channel, and is located on an inner side of the metal net, so as to be configured to prevent the metal net from moving towards a proximal end of the surgical channel.

7. The channel device for surgery according to claim 4, wherein the puncture head is provided with an injection hole communicating the surgical channel and an exterior; and
   the conveyor further comprises a supporting tube and a Luer taper, wherein the supporting tube is arranged within the surgical channel, and a distal end of the supporting tube is in connection with the puncture head and is in communication with the injection hole; and
   the Luer taper is in communication with the supporting tube.

8. The channel device for surgery according to claim 1, wherein the conveyor further comprises a snap ring, wherein the snap ring is in connection with the binding wire, so as to be configured to pull the binding wire away from the binding cord under an action of an external force.

9. The channel device for surgery according to claim 8, wherein the conveyor further comprises a clamping portion, and the snap ring is configured to be clamped with or disengaged from the clamping portion, when the snap ring is disengaged from the clamping portion, the snap ring is configured to pull the binding wire away from the binding cord under an action of an external force.

10. The channel device for surgery according to claim 9, wherein the clamping portion is column-shaped; and
the snap ring comprises a semicircular ring and a toggle handle which are in connection with each other, wherein the semicircular ring is configured to be clamped with or disengaged from an external wall of the clamping portion.

11. The channel device for surgery according to claim 1, wherein the conveyor further comprises an outer tube and a trigger structure, wherein the trigger structure comprises a trolley, a trigger, and a handle, wherein the trigger and the trolley are commonly slidably arranged on the handle, the trolley is in connection with the outer tube, and the outer tube is driven to move so as to open the surgical channel when the trolley slides relative to the handle;
the trolley is provided with a first engaging portion and a second engaging portion; the trigger is provided with a plurality of first locking portions; and the handle is provided with a plurality of second locking portions,
wherein different first locking portions are configured to cooperate with the first engaging portion, so as to drive the trolley to slide intermittently relative to the handle, such that the second engaging portion cooperates with different second locking portions, hereby locking, into different positions on the handle, the trolley being sliding.

12. The channel device for surgery according to claim 11, wherein each of the first locking portions is configured to be in locking cooperation with the first engaging portion, when the trigger slides relative to the handle in a first direction, such that the trigger pushes the trolley to slide in the first direction; and
each of the first locking portions is configured to be in slidable cooperation with the first engaging portion, when the trigger slides relative to the handle in a second direction, wherein the trolley is fixed relative to the handle, when one of the first locking portions is in slidable cooperation with the first engaging portion,
wherein the first direction is opposite to the second direction.

13. The channel device for surgery according to claim 12, wherein the trigger structure further comprises a reset member,
wherein the reset member is connected between the trigger and the handle, such that the trigger has a tendency to slide relative to the handle in the second direction.

14. The channel device for surgery according to claim 13, wherein each of the first locking portions is a first unidirectional tooth arranged to protrude from the trigger; and each of the second locking portions is a second unidirectional tooth arranged to protrude from the handle.

15. The channel device for surgery according to claim 14, wherein the first engaging portion is a first elastic piece, with one end of the first elastic piece being connected on the trolley, while another end of the first elastic piece being configured to be in locking cooperation with the first unidirectional tooth when moving in the first direction, and to be in slidable cooperation with the first unidirectional tooth when moving in the second direction; and
the second engaging portion is a second elastic piece, with one end of the second elastic piece being connected on the trolley, while the other end of the second elastic piece being configured to be in locking cooperation with the second unidirectional tooth when moving in the first direction, and to be in slidable cooperation with the second unidirectional tooth when moving in the second direction.

16. A trigger structure, comprising:
a trolley, a trigger, and a handle, wherein the trigger and the trolley are commonly slidably arranged on the handle; and
the trolley is provided with a first engaging portion and a second engaging portion; the trigger is provided with a plurality of first locking portions; and the handle is provided with a plurality of second locking portions,
wherein different first locking portions are configured to cooperate with the first engaging portion, so as to drive the trolley to slide intermittently relative to the handle, such that the second engaging portion cooperates with different second locking portions, hereby locking the trolley in sliding in different positions on the handle.

17. The trigger structure according to claim 16, wherein each of the first locking portions is configured to be in locking cooperation with the first engaging portion, when the trigger slides relative to the handle in a first direction, such that the trigger pushes the trolley to slide in the first direction; and
each of the first locking portions is configured to be in slidable cooperation with the first engaging portion, when the trigger slides relative to the handle in a second direction, wherein the trolley is fixed relative to the handle, when one of the first locking portions is in slidable cooperation with the first engaging portion,
wherein the first direction is opposite to the second direction.

18. The trigger structure according to claim 17, wherein the trigger structure further comprises a reset member,
wherein the reset member is connected between the trigger and the handle, such that the trigger has a tendency to slide relative to the handle in the second direction.

19. The trigger structure according to claim 18, wherein each of the first locking portions is a first unidirectional tooth arranged to protrude from the trigger; and each of the second locking portions is a second unidirectional tooth arranged to protrude from the handle.

20. The trigger structure according to claim 19, wherein the first engaging portion is a first elastic piece, with one end of the first elastic piece being connected on the trolley, while another end of the first elastic piece being configured to be in locking cooperation with the first unidirectional tooth when moving in the first direction, and to be in slidable cooperation with the first unidirectional tooth when moving in the second direction; and the second engaging portion is a second elastic piece, with one end of the second elastic piece being connected on the trolley, while the other end of the second elastic piece being configured to be in locking cooperation with the second unidirectional tooth when moving in the first direction, and to be in slidable cooperation with the second unidirectional tooth when moving in the second direction.

* * * * *